US008450337B2

(12) United States Patent
Priebe et al.

(10) Patent No.: US 8,450,337 B2
(45) Date of Patent: May 28, 2013

(54) METHODS OF TREATING SKIN DISORDERS WITH CAFFEIC ACID ANALOGS

(75) Inventors: Waldemar Priebe, Houston, TX (US); Charles Conrad, Spring, TX (US); Timothy Madden, Sugar Land, TX (US)

(73) Assignee: Moleculin, LLC, Houston, TX (US)

( * ) Notice: Subject to any disclaimer, the term of this patent is extended or adjusted under 35 U.S.C. 154(b) by 341 days.

(21) Appl. No.: 12/570,819

(22) Filed: Sep. 30, 2009

(65) Prior Publication Data

US 2010/0152143 A1   Jun. 17, 2010

Related U.S. Application Data

(60) Provisional application No. 61/101,589, filed on Sep. 30, 2008.

(51) Int. Cl.
*A61K 31/44* (2006.01)
*A61K 31/16* (2006.01)
*A61K 31/275* (2006.01)
*A61P 17/06* (2006.01)

(52) U.S. Cl.
USPC .......... 514/277; 514/863; 514/18.6; 514/390; 514/392; 558/390; 558/392

(58) Field of Classification Search
None
See application file for complete search history.

(56) References Cited

U.S. PATENT DOCUMENTS

| | | | |
|---|---|---|---|
| 5,614,215 A | 3/1997 | Ribier et al. | |
| 5,616,332 A | 4/1997 | Herstein | |
| 5,719,129 A | 2/1998 | Andary et al. | |
| 5,719,195 A | 2/1998 | Braiman | |
| 5,932,234 A | 8/1999 | Simon et al. | |
| 5,981,583 A | 11/1999 | Aggarwal et al. | |
| 6,121,243 A | 9/2000 | Lanzendorfer et al. | |
| 6,313,165 B1 | 11/2001 | Grunberger et al. | |
| 6,469,063 B1 | 10/2002 | Bleich et al. | |
| 6,492,429 B1 | 12/2002 | Graus et al. | |
| 6,689,811 B2 | 2/2004 | Koumenis et al. | |
| 6,703,031 B1 | 3/2004 | Iwasaki et al. | |
| 6,800,659 B2 * | 10/2004 | Roifman et al. | 514/521 |
| 6,803,382 B2 | 10/2004 | Eustache et al. | |
| 6,831,106 B1 | 12/2004 | Bernardon et al. | |
| 7,005,274 B1 | 2/2006 | Terkeltaub et al. | |
| 7,745,468 B2 | 6/2010 | Priebe et al. | |
| 7,807,719 B2 | 10/2010 | Roifman et al. | |
| 2002/0102249 A1 | 8/2002 | Denholm et al. | |
| 2004/0228871 A1 | 11/2004 | Hasan et al. | |
| 2004/0258765 A1 | 12/2004 | Gee | |
| 2004/0259816 A1 | 12/2004 | Pandol et al. | |
| 2005/0271661 A1 | 12/2005 | Manivasakam et al. | |
| 2005/0277680 A1 | 12/2005 | Priebe et al. | |
| 2006/0058297 A1 | 3/2006 | Roifman et al. | |
| 2007/0232668 A1 | 10/2007 | Priebe et al. | |
| 2008/0167277 A1 | 7/2008 | Conrad et al. | |
| 2009/0163545 A1 | 6/2009 | Goldfarb | |
| 2010/0152143 A1 | 6/2010 | Priebe et al. | |

FOREIGN PATENT DOCUMENTS

| | | |
|---|---|---|
| DE | 1212984 B | 3/1966 |
| DE | 4330105 A1 | 3/1993 |
| JP | 41003540 B4 | 3/1966 |
| WO | 9005109 A1 | 2/1990 |
| WO | 03073999 A2 | 9/2003 |
| WO | 03086396 A1 | 10/2003 |
| WO | 2005000777 A2 | 1/2005 |
| WO | 2005092904 A1 | 1/2005 |
| WO | 2005058829 A1 | 6/2005 |
| WO | 2006029515 A1 | 3/2006 |
| WO | 2006057824 A2 | 6/2006 |
| WO | 2006086422 A2 | 8/2006 |
| WO | WO-2006091837 A2 | 8/2006 |
| WO | 2007006143 A1 | 1/2007 |
| WO | 2007115269 A2 | 10/2007 |
| WO | 2007130523 A2 | 11/2007 |
| WO | 2008005954 A2 | 1/2008 |
| WO | 2008079460 A2 | 7/2008 |
| WO | 2008083389 A1 | 7/2008 |
| WO | 2008118445 A1 | 10/2008 |
| WO | 2008121858 A1 | 10/2008 |
| WO | 2009073575 A2 | 6/2009 |
| WO | 2009091150 A2 | 7/2009 |
| WO | 2009091506 A2 | 7/2009 |
| WO | 2010081158 A2 | 7/2010 |

OTHER PUBLICATIONS

Robert P. Sheridan. The Most Common Chemical Replacements in Drug-Like Compounds. J. Chem. Inf. Comput. Sci. 2002, 42, 103-108.*
Bors, Wolf, et al., Antioxidant Mechanisms of Polyphenolic Caffeic Acid Oligomers, Constituents of *Salvia officinalis*, Biol Res 37, 2004, pp. 301-311.
Da Cunha, Fernanda M., et al., "Caffeic Acid Derivatives: In Vitro and In Vivo Anti-inflammatory Properties", Free Radical Research, published by Taylor & Francis, vol. 38, No. 11, Nov. 2004, pp. 1241-1253.
Darnell, James E. Jr., "Validating Stat3 in cancer therapy", Nature Medicine, vol. 11, No. 6, Jun. 2005, pp. 595-596.

(Continued)

*Primary Examiner* — Frederick Krass
*Assistant Examiner* — Michael P Cohen
(74) *Attorney, Agent, or Firm* — Dennis A. Bennett; Michael Sertic

(57) ABSTRACT

Embodiments of the invention generally relate to pharmaceutical compositions containing at least one caffeic acid compound and methods for the topical treatment of proliferative and inflammatory skin disorders such as plaque psoriasis, atopic dermatitis, and other disorders. In some embodiments, the topical treatment includes applications of the pharmaceutical composition containing at least one caffeic acid compound or a mixture of caffeic acid compounds such as caffeic acid ester compounds, caffeic acid amide compounds, analogues thereof, derivatives thereof, salts thereof, or mixtures thereof. The pharmaceutical composition or topical dosage may contain the caffeic acid compound at a concentration by weight within a range from about 0.01% to about 20%, preferably, from about 0.1% to about 15%, preferably, from about 1% to about 10%, more preferably, from about 3% to about 7%, and more preferably, from about 4% to about 6%.

6 Claims, No Drawings

OTHER PUBLICATIONS

Frenkel, Krystyna, et al., "Caffeic Acid Phenethyl Ester (CAPE): Inhibitor of Cataracts and Other Diseases Resulting from Oxidative Stress", NYU/NYU School of Medicine, Office of Industrial Liaison/Technology Transfer, http://www.med.nyu.edu/oil/tech/therapeutics/frenkel2.html, dated Dec. 28, 2006.
International Search Report and Written Opinion dated Apr. 29, 2008, International Application No. PCT/US07/89235.
Irina Kirillova et al., "Tumor Necrosis Factor Induces DNA Replication in Hepatic Cells through Nuclear Factor κB Activation," Cell Growth and Differentiation, Dec. 1999, 10(12):819-828.
K. Natarajan et al., "Caffeic Acid Phenethyl Ester is a Potent and Specific Inhibitor of Activation of Nuclear Transcription Factor NF κB," Proc. Natl. Acad. Sci. USA, Aug. 1996, 93(17):9090-9095.
Levy, David E., et al., "What does Stat3 do?", The Journal of Clinical Investigation, May 2002, vol. 109, No. 9, pp. 1143-1148.
Natarajan, K., et al., "Caffeic acid phenethyl ester is a potent and specific inhibitor of activation of nuclear transcription factor NF-kappa B.", Proc Natl Acad Sci U.S.A., Aug. 20, 1996, 93(17):9090-5.
Sano, Shigetoshi, et al., "Signal Transducer and Activator of Transcription 3 Is a Key Regulator of Keratinocyte Survival and Proliferation following UV Irradiation," Cancer Research 2005; 65: (13), Jul. 1, 2005, pp. 5720-5729.
Seidel, H. Martin, et al., "Pharmaceutical intervention in the JAK/STAT signaling pathway", Oncogene, Macmillan Publishers Ltd. (2000), 19, 2645-2656.
Shigetoshi Sano et al., "Stat3 Links Activated Keratinocytes and Immunocytes Required for Development of Psoriasis in a Novel Transgenic Mouse Model," Nature Medicine, Jan. 2005, 11(1):43-49.
Yu, Hua, et al., "The Stats of Cancer—New Molecular Targets Come of Age", Nature Reviews | Cancer, Nature Publishing Group, vol. 4, Feb. 2004, pp. 97-105.
Darnell, J.E. Jr. (2005), Validating Stat3 in Cancer, Nature Medicine, vol. 11, No. 6, 595-596.
Heinrich. P.C. et al., (1998) Interleukin-6-Type Cytokine Signaling Through the GPI3O/Jak/ISTAT Pathway1, Biochem J. 334. 297-314.
Seidel. H. M. et at., (2000) Pharmaceutical Interventionin the JAK/STAT Signaling Pathway, Oncogene, 19, 2645-2656.
Liu, H., et al., (2006) Immunohistochemical Localization of Activated Stat3 and hTERT Protein in Psoriasis Vulgaris, Eur J Dermatol 16(2): 205-6.
Trajkovski, T., STAT3-.A Promising Molecular Target for Cancer Therapy, University of Toronto Medical Journal, 16.
Pardanani, A., (2007) JAK2 Inhibitor Therapy in Myeloproliferative Disorders : Rationale, Preclinical studies and Ongoing Clinical Trials, Leukemia, 22, 23-30.
Yu, Hua, et aL, (2004) The STATs of Cancer—New Molecular Targets Come of Age, Nature Reviews, vol. 4. 97-105.
Tefferi, A.. et al., (2005) JAK2 in Myeloproliferative Disorders is Not Just Another Kinase, Cell Cycle, 4:8, 1053-1056.
Levy, D.E., et al., (2002) What does Stat3 Do? The Journal of Clinical Investigation, vol. 109, No. 9.
Nikitakis, N.G. et al., (2004) Targeting the STAT Pathway in Head and Neck Cancer: Recent Advances Future Prospects, Current Cancer Drug Targets, 4, 637-651.
Sun, J., et al., (2005) Cucurbitacin Q: A Selective STAT3 Activation Inhibitor with Potent Antitumor activity, Oncogene 24, 3236-3245.
Rahaman, S.0 et al., (2002) Inhibition of Constitutively Active Stat3 Suppresses Proliferation and induces Apoptosis in Glioblastoma Multiforme Cells, Oncogene, 21, 8404-8413.
Xie, T.. et al., (2004) Stat3 Activation Regulates the Expression of Matrix Metalloproteinase-2 and Tumor Invasion and Metastasis, Oncogene, 23, 3550-3560.
Huang, S., (2007) Regulation of Metastases by Signal Transducer and Activator of Transcription3 Siggnaling Pathway: Clinical Implications, Clin Cancer Res 13(5) 1362-1366.
Xie, T., et at., (2006) Activation of Stat3 in Human Melanoma Promotes Brain Metastasis, Cancer RE'S, 66:(6), 3188-3196.
Levy, D.E., et al., (2006) STAT3: A Multifaceted Oncogene, PNAS, vol. 103, No. 27, 10151-10152.

Kisseleva, T. et al., (2002) Signaling Through the JAK/STAT Pathway, Recent Advances and Future Challenges, Gene 285: 1-24.
Chen, X., et al., (1998) Crystal Structure of a Tyrosine Phosphorylated STAT-I Dimer Bound to DNA, Cell 93: 827-839.
Song, J.I., et (2000) STAT Signaling in Head and Neck Cancer, Oncogene, 19: 2489-2495.
Kijima, T. et al., (2002) STAT3 Activation Abrogates Growth Factor Dependence and Contributes to Head and Neck Squamous Cell Carcinoma Tumor Growth in Vivo, Cell Growth Differ, 13: 355-362.
Song, L et al., (2003) Activation of Stat3 by Receptor Tyrosine Kinases and Cytokines Regulates Survival in Human Non-Small Cell Carcinoma Cells, Oncogene, 22: 4150-4165.
Gadina, M., et al,,(2001) Signaling by Type I and Type II Cytokine Receptors: Ten Years After,Curr. Opin. Immunol. 13:363.
Horvath, C.M. (2004) The Jak-STAT Pathway Stimulated by Interferon Gamma, Science, STKE, 260 tr8.
Lai, S.Y., et al., (2005) Erythropoietin-Mediated Activation of JAK-STAT Signaling Contributes to Cellular Invasion in Head and Neck Squamous Cell Carcinoma, Oncogene, 24: 4442-4449.
Siavash, H., et al., (2004) Abrogation ofIL-6-Medlateci JAK Signalling by the Cyclopentenone Prostaglandin 15d-PGJ (2) in Oral Squamous Carcinoma Cells, British J of Cancer, 91 : 1074-1080.
Quadros, M.R., at al., (2004) Complex Regulation of Signal Transducers and Activators of Transcription 3 Activation in Normal and Malignant Keratinocytes, Cancer Res, 64 :3934-3939.
Hebenstreit D. et al., (2005) JAK/STAT-Dependent Gene Regulation by Cytokines, Drug News Perspect. vol. 18 (4), pp. 243-249.
Boulton, TG, et al., (1995) STAT3 Activation by Cytokines Utilizing gpI3O and Related Transducers Involves a Secondary Modification Requiring an H7-Sensitive Kinase Proc Natl Acad Sci U S A. 92(15): 6915-6919.
Yuan ZL et al., (2004) Central Role of the Threonine Residue within the p+1 Loop of Receptor Tyrosine Kinase in STAT3 Constitutive Phosphorylation in Metastatic Cancer Cells, Mol. Cell Biol. vol. 24 (21), pp. 930-9400.
Silva C.M. (2004) Role of Stats as Downstream Signal Transducers In Src Family Kinase-Mediated Tumorigenesis Oncogene vol. 23 (48), pp. 8017-8023.
O'shea, J. L et al., (2004) A New Modality for Immunosuppression: Targeting the JAK/STAT Pathway, Nature Rev. Drug Disc. (3): 555-584.
Hellgren, G.,et al., (1999) The Growth Hormone Receptor Associates with Jaki Jak2 and Tyk2 in Human Liver, Growth Horm. IGF Res. 9(3):212-8.
Krebs, L et al., (2001) SOCS Proteins: Negative Regulators of Cytàkine Signaling Stem Cells vol. 19, pp. 378-387.
Shuai, K (2006) Regulation of Cytokine Signaling Pathways by PIAS Proteins, Cell Research, vol. 16 (2), pp. 196-202.
Leaman, D. W, et al., (1996) Roles of JAKs in Activation of STATs and Stimulation of c-fos Gene Expression by Epidermal Growth Factor, Mol Cell Biol. 16(1): 369-375.
Horiguchi, A. et al, (2010) STAT3 Inhibitor WPIOG6 As a Novel Therapeutic Agent for Renal Cell Carcinoma, British Journal of Cancer,102(11), 1592-I599CODEN: BJCAAI;ISSN: 0007-0920.
Kupferman, Michael, E. et al., (2009) Therapeutic Suppression of Constitutive and Inducible JAK/STAT Activation In Head And Neck Squamous Cell Carcinoma, Journal of Experimental Therapeutics and Oncology 8(2), 117-127 CODEN: JETOFX; ISSN: 1359-4117.
Kong, Ling-Yuan, et ai., (2009) A Novel Phosphorylated STAT3 inhibitor Enhances T Cell Cytotoxicity Against Melanoma Through Inhibition Of Regulatory T Cells , Cancer Immunology Immunotherapy, 58(7), 1023-1032 CODEN: CIIMDN; ISSN: 0340-7004.
Kong, Ling-Yuan, et al,(2008) A Novel Inhibitor of Signal Transducers and Activators of Transcription 3 Activation Is Efficacious Against Established Central Nervous System Melanoma and Inhibits Regulatory T Cells Clinical Cancer Research, 14(18), 5759-5768 CODEN: CCREF4; ISSN: 1078-0432.
Verstovsek, Srdan, et al, (2008) WP1066, a Novel JAK2 Inhibitor, Suppresses Proliferation and Induces Apoptosis in Erythroid Human Cells Carrying the JAK2 V617F Mutation Clinical Cancer Research 14(3), 788-796 CODEN: CCREF4; ISSN: 1078-0432.

Ferrajoli, Alessandra, et al, (2007) WP1066 Disrupts Janus Kinase-2 and Induces Caspase-Dependent Apoptosis in Acute Myelogenous Leukemia Cells, Cancer Research, 67(23), 11291-11299 CODEN: CNREA8; ISSN: 0008-5472.

Hussain, S. Farzana, et al, (2007) A Novel Small Molecule Inhibitor of Signal Transducers and Activators of Transcription 3 Reverses Immune Tolerance in Malignant Glioma Patients, Cancer Research, 67(20), 9630-9636 Coden: CNREA8; ISSN: 0008-5472.

Bartholomeusz, Geoffrey, et al,(2007) Degrasyn Activates Proteasomal-Dependent Degradation of C-Myc, Cancer Research, 67(8), 3912-3918 CODEN: CNREA8; ISSN: 0008-5472.

Iwamaru, A., et al., (2007) A Novel Inhibitor of the STAT3 Pathway Induces Apoptosis in Malignant Glioma Cells both in Vitro and In Vivo, Oncogene, 26(17), 2435-2444 CODEN: ONCNES; ISSN: 0950-9232.

Schepetkin, Igor A., et al, (2006) Novel Small-Molecule Inhibitors of Anthrax Lethal Factor Identified by High-Throughput Screening, Journal of Medicinal Chemistry, 49(17), 5232-5244 CODEN: JMCMAR; ISSN: 0022-2623.

Duque, J., et al.,(1996) Structure of N-benzyl-[2-cyano-3-(7-furyl) acrylarnide], Revista CENIC, Ciencias Quimicas, 27 (1-2-3), 25-29 CODEN: RCCQER; ISSN: 1015-8553.

Hernandez, Ramon, et al, (1996) 2-Cyano-N-furfuryl-3-(2-furyl)acrylamide, Acta Crystallographica Section C: Crystal Structure Communications, C52(1), 203-5 CODEN: ACSCEE; ISSN: 0108-2701.

Pomes, R., et al, (1994) Structure of N-(2-furfuryl)-2-cyano-3-(5-nitro-2-furyl)acrylamide, Anales de la Asociacion Quimica Argentina, 82(4), 249-55 CODEN: AAQAAE; ISSN: 0365-0375.

Durruthy, 0., et al, (1993) Structure f N-(2-furylmethyl)-alpha-cyano-2-furanacrylamide, Acta Cirystallographica, Section C: Crystal Structure Communications, C49(3), 558-9 CODEN: ACSCEE; ISSN: 0108-2701.

Saikachi, Haruo, et al., (1959) Synthesis of furan derivatives. XVIII. 2-Cyano-3(5-nitro-2-furyl) acrylamides and esters, Chem. & Pharm. Bull. (Tokyo), 7, 453-6.

EPO Communication Extended Supplementary Search Report and Search Opinion EP 09 794 969.7, Mar. 16, 2012.

International Preliminary Report on Patentability WO2010005807, Jan. 11, 2011.

* cited by examiner

METHODS OF TREATING SKIN DISORDERS WITH CAFFEIC ACID ANALOGS

CROSS-REFERENCE TO RELATED APPLICATION

This application claims benefit of U.S. Ser. No. 61/101,589, filed Sep. 30, 2008, which is incorporated herein by reference in its entirety.

BACKGROUND OF THE INVENTION

1. Field of the Invention

Embodiments of the invention generally relate to treating proliferative and inflammatory skin disorders and to the compositions utilized during the treatment.

2. Description of the Related Art

Many different skin diseases or disorders relate to persistent inflammation and abnormal cell growth. For example, psoriasis affects an estimated two to three percent of the world's population of which, plaque psoriasis (psoriasis vulgaris) comprises about 80 percent of these cases. Plaque psoriasis is characterized by raised, red inflamed lesions covered by a silvery white scale comprised of dead skin cells. Other forms of psoriasis include inverse psoriasis, pustular psoriasis, erythrodermic psoriasis, and guttate psoriasis. The lesions from psoriasis make the disorder both a medical and a cosmetic problem.

However, current topical treatments for psoriasis fail to produce satisfactory results. Prior treatments often take away some inflammation but do not cure or eliminate the disorder. Further, patients on such treatment may achieve only some improvement in their condition over long periods of several months.

Therefore, there exists a need for an improved topical composition and method for treating proliferative and inflammatory skin disorders such as plaque psoriasis, atopic dermatitis and other disorders.

SUMMARY OF THE INVENTION

Embodiments of the invention generally relate to pharmaceutical compositions containing at least one caffeic acid compound and methods for the topical treatment of proliferative and inflammatory skin disorders such as cutaneous T-cell lymphoma, plaque psoriasis, atopic dermatitis, and other skim disorders. In some embodiments, the topical treatment includes applications of the pharmaceutical composition containing at least one caffeic acid compound or a mixture of caffeic acid compounds such as caffeic acid ester compounds, caffeic acid amide compounds, analogues thereof, derivatives thereof, salts thereof, or mixtures thereof. Exemplary caffeic acid ester compounds include caffeic acid phenethyl ester (CAPE), caffeic acid benzyl ester (CABE), analogues thereof, derivatives thereof, salts thereof, or mixtures thereof.

In some embodiments, the pharmaceutical composition or topical dosage may contain the caffeic acid ester compound at a concentration by weight within a range from about 0.01% to about 20%, preferably, from about 0.1% to about 15%, preferably, from about 1% to about 10%, more preferably, from about 3% to about 7%, and more preferably, from about 4% to about 6%. In some examples, the topical pharmaceutical composition contains the caffeic acid ester compound at a concentration of about 5% by weight. In one example, the topical pharmaceutical composition contains CAPE at a concentration of about 5% by weight. In another example, the topical pharmaceutical composition contains CABE at a concentration of about 5% by weight.

In one embodiment, a method for treating proliferative skin disorders is provided which includes applying a topical pharmaceutical composition to a lesion, wherein the topical pharmaceutical composition comprises a caffeic acid amide compound having the generic chemical structure of:

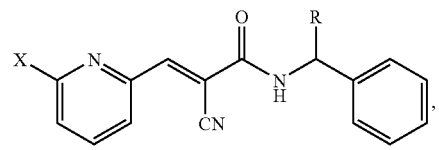

where X is a halogen and R is hydrogen, hydroxyl, alkyl, alkoxy, $C_3$-$C_7$-cycloalkyl, $C_6$-$C_{10}$-aryl, $C_7$-$C_{10}$-aralkyl, heteroatom-substituted or heteroatom-unsubstituted, isomers thereof, or derivatives thereof, and the topical pharmaceutical composition comprises the caffeic acid amide compound at a concentration by weight within a range from about 0.01% to about 20%.

In one example, the caffeic acid amide compound has the chemical structure of:

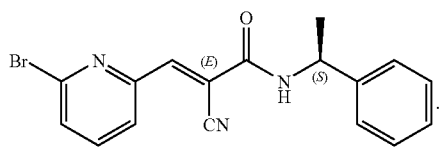

In another example, the caffeic acid amide compound has the chemical structure of:

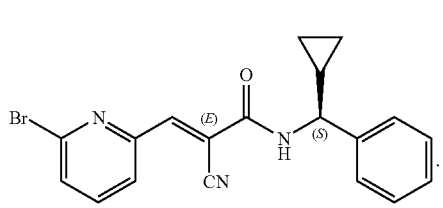

In another example, the caffeic acid amide compound has the chemical structure of:

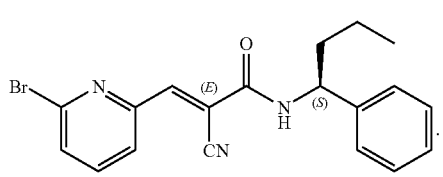

In another embodiment, a method for treating proliferative skin disorders is provided which includes applying a topical pharmaceutical composition to a lesion, wherein the topical pharmaceutical composition comprises a caffeic acid amide compound having the chemical structure of:

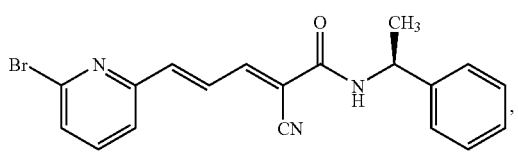 [SMILES: C[C@H](NC(=O)/C(C#N)=C/C=C/c1cccc(Br)n1)c1ccccc1]

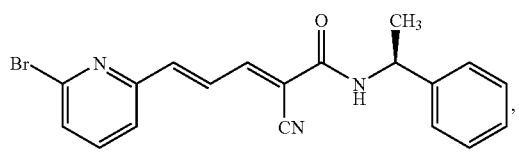

and the topical pharmaceutical composition comprises the caffeic acid amide compound at a concentration by weight within a range from about 0.01% to about 20%.

In some embodiments, the topical pharmaceutical composition or topical dosage may contain the caffeic acid amide compound at a concentration by weight within a range from about 0.01% to about 20%, preferably, from about 0.1% to about 15%, preferably, from about 1% to about 10%, more preferably, from about 3% to about 7%, and more preferably, from about 4% to about 6%. In one example, the topical pharmaceutical composition contains the caffeic acid amide compound at a concentration of about 5% by weight.

The topical pharmaceutical composition containing the caffeic acid compound may further contain at least one mechanistic compound. Useful mechanistic compounds include cell differentiating agents, anti-proliferative agents, mitochondrial inhibitors, topical steroids, immunosuppressive compounds, JAK2 inhibitors, JAK3 inhibitors, parathyroid hormone-related protein (PTHrP) agonists, cell adhesion blockers, derivatives thereof, or combinations thereof. In some examples, the topical pharmaceutical composition may also contain retinoic acid, retinoic acid derivatives, vitamin D, or vitamin D analogs—which may be used as a cell differentiating agent.

In another embodiment, a method for treating a skin disorder provides applying the topical pharmaceutical composition on lesions multiple times daily until symptoms of the disorder disappear.

In another embodiment, a pharmaceutical composition for topical application to psoriatic lesions is provided which includes a carrier suitable for topical administration, and a caffeic acid amide compound having the generic chemical structure of:

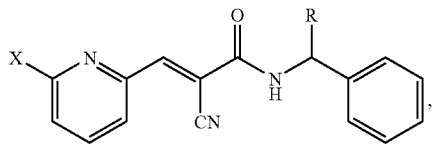

where X is a halogen and R is hydrogen, hydroxyl, alkyl, alkoxy, $C_3$-$C_7$-cycloalkyl, $C_6$-$C_{10}$-aryl, $C_7$-$C_{10}$-aralkyl, heteroatom-substituted or heteroatom-unsubstituted, isomers thereof, or derivatives thereof, and the caffeic acid amide compound is at a concentration by weight within a range from about 0.01% to about 20% of the pharmaceutical composition.

In another embodiment, the pharmaceutical composition for topical application to psoriatic lesions is provided which includes a carrier suitable for topical administration, and a caffeic acid amide compound having the chemical structure of:

and the caffeic acid amide compound is at a concentration by weight within a range from about 0.01% to about 20% of the pharmaceutical composition.

In some embodiments, the pharmaceutical composition may further contain petroleum jelly or dimethyl sulfoxide. Also, the caffeic acid compound may be an analogue, a derivative, or a salt of a caffeic acid or a caffeic acid amide compound.

DETAILED DESCRIPTION

Embodiments of the invention generally relate to pharmaceutical compositions containing at least one caffeic acid compound and methods for the topical treatment of proliferative and inflammatory skin disorders such as cutaneous T-cell lymphoma, plaque psoriasis, atopic dermatitis, and other disorders with a topical application of the pharmaceutical composition. Caffeic acid compounds as an active agent may include caffeic acid ester compounds, caffeic acid amide compounds, analogues thereof, derivatives thereof, salts thereof, or mixtures thereof.

According to one embodiment, the pharmaceutical composition contains at least one caffeic acid ester compound or a mixture of caffeic acid ester compounds as an active agent. In one example, the caffeic acid ester compound is caffeic acid phenethyl ester (CAPE). In another example, the caffeic acid ester compound is caffeic acid benzyl ester (CABE). CAPE and CABE have the following chemical structures:

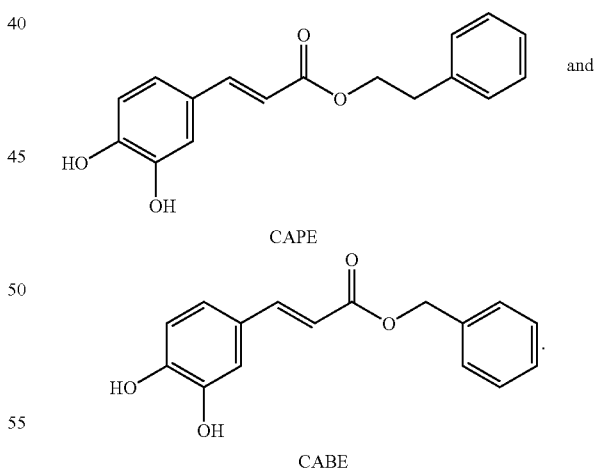

In other examples, the pharmaceutical composition may contain analogues, derivatives, salts, or mixtures of CAPE, CABE, or other caffeic acid ester compounds useful as the active agent.

In another embodiment, the pharmaceutical composition contains at least one caffeic acid amide compound or a mixture of caffeic acid amide compounds as an active agent. In one example, the caffeic acid amide compound has the chemical structure 1:

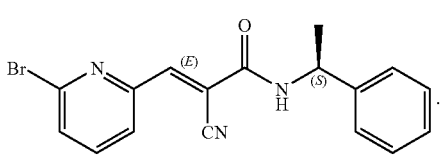

(1)

In another example, the caffeic acid amide compound has the chemical structure 2:

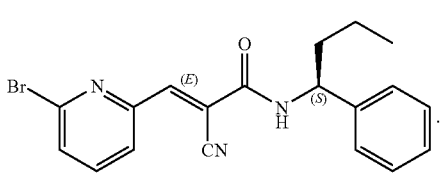

(2)

In another example, the caffeic acid amide compound has the chemical structure 3:

(3)

In another example, the caffeic acid amide compound has the chemical structure 4:

(4)

In other examples, the pharmaceutical composition may contain analogues, derivatives, salts, or mixtures of caffeic acid amide compounds having the chemical structures 1, 2, 3, or 4 and useful as the active agent during the treatments described herein.

In other embodiments, the pharmaceutical composition may contain other caffeic acid amide compounds which are useful as active agents. The caffeic acid amide compounds may have a generic chemical structure, such as the chemical structure 5:

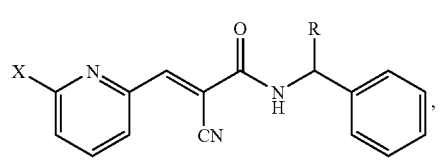

(5)

where X is a halogen and R is hydrogen, hydroxyl, alkyl, alkoxy, $C_3$-$C_7$-cycloalkyl, $C_6$-$C_{10}$-aryl, $C_7$-$C_{10}$-aralkyl, heteroatom-substituted or heteroatom-unsubstituted, isomers thereof, or derivatives thereof. In some examples, R is an alkyl group of $C_1$-$C_{12}$, including methyl, ethyl, propyl, butyl, amyl, isomers thereof, or derivatives thereof. The chemical structure 5 has stereochemistry about the carbon atom which is bonded to the R group. In one embodiment, the S-enantiomer of chemical structure 5 may be used as the active agent. In other examples, the pharmaceutical composition may contain analogues, derivatives, salts, or mixtures of caffeic acid amide compounds having the chemical structure 5 and useful as the active agent.

In other embodiments, the pharmaceutical composition may have other caffeic acid compounds which are useful as active agents. The caffeic acid compounds may have a more generic chemical structure, such as the chemical structure 6:

(6)

and pharmaceutically acceptable salts thereof, where $R_1$, $R_2$, $R_3$, $R_6$, $R_7$, $R_8$, or $R_9$ are independently selected from H, OH, $NO_2$, $N_3$, $NH_2$, alkyl, alkoxy, O-acyl, COOH, F, Cl, Br, I, or derivatives thereof; $R_4$ is H, CN, or $SO_2R$; $X_1$ is O, NH, or S; and $R_5$ is H, alkyl, alkoxy, cycloakyl, O-acyl, N-alkyl, N-acyl, or alkylamine. Alkyl groups usually have from 1 to 12 carbon atoms and include methyl, ethyl, propyl, butyl, amyl, isomers thereof, or derivatives thereof. In some examples, the alkyl groups may have from 1 to 6 carbon atoms. In other examples, the alkyl groups may have from 1 to 4 carbon atoms. The alkyl group may be optionally substituted with 1-3 substituents such as hydroxyl, alkylamine, —O-alkyl, acyl, —O-acyl, —N(R)-acyl, —C(O)—O-alkyl, —C(O)—N(R)-alkyl, thiol, and halo, where R is hydrogen or alkyl. Suitable alkyl groups include methyl, isopropyl, —$CH_2$-cyclohexyl, and cyclopropyl.

The chemical structure 6 has stereochemistry about the carbon atom which is bonded to the $R_5$ group. In one embodiment, the S-enantiomer of chemical structure 6 may be used as the active agent. In other examples, the pharmaceutical composition may contain analogues, derivatives, salts, or mixtures of caffeic acid amide compounds having the chemical structure 6 and useful as the active agent.

The term "$SO_2R$", where R is an alkyl group, refers to the group —$SO_2$— alkyl.

The term "alkanol" refers to the group -alkyl substituted with 1-3 hydroxy groups.

The term "alkylamine" refers to the group -alkyl substituted with 1-3 —$NR_2$ groups, wherein each R group may be independently H and/or alkyl.

The term "acyl" refers to —C(O)—R where R is alkyl.

The term "cyclic alkyl" or "cycloalkyl" refers to alkyl groups that are cyclic. Cycloalkyl groups may have 3 to 12 carbon atoms. In some embodiments, the cycloalkyl groups may have 3 to 6 carbon atoms. In some embodiments, the cycloalkyl groups may have 3 to 4 carbon atoms. The cycloalkyl group may be optionally substituted with 1-3 substituents include hydroxyl, alkylamine, —O-alkyl, acyl, —O-acyl, —N(R)-acyl, —C(O)—O-alkyl, —C(O)—N(R)-alkyl, thiol, and halo, where R is H or alkyl. Suitable cyclic groups include cyclohexyl, cyclopentyl, and cyclopropyl.

The term "pharmaceutically acceptable salt" includes salts of the aforementioned compounds and prodrugs derived from the combination of a compound as set forth herein and an organic acid, an inorganic acid, or a base. Suitable acids include hydrogen chloride (HCl).

The following reaction illustrates synthesis of CAPE:

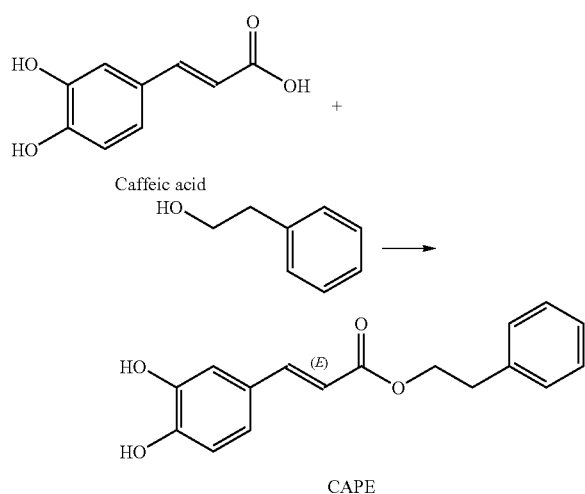

CAPE

As shown, the general synthetic approach to CAPE and its analogs involves formation of an ester bond of caffeic acid or its analogs with phenyl derivatives containing a hydroxy group. The caffeic acid ester compounds may be synthesized by utilizing various methods of ester formation which leads to formation of an ester bond between caffeic acid and its analogs and respective alcohols. For example, Fischer Esterification (Fischer-Speier Esterification) utilizes a Lewis or Brønstedt acid-catalyzed esterification of carboxylic acids with alcohols to give esters via a reaction in which the products and reactants are in equilibrium, as may be influenced by either removing one product from the reaction mixture (for example, removal of the water by azeotropic distillation or absorption by molecular sieves) or by employing an excess of one reactant. Alternative reactions employ coupling reagents such as dicyclohexylcarbodiimide (Steglich Esterification), preformed esters (transesterification), carboxylic acid chlorides or anhydrides. Esters may also be produced by oxidations, such as by the Baeyer-Villiger oxidation and oxidative esterifications. Similar procedures can be used to make the analogs.

The caffeic acid compounds as described in embodiments herein represent suitable active agents for topical application to treat skin disorders or diseases. Caffeic acid compounds may include caffeic acid ester compounds, caffeic acid amide compounds, analogues thereof, derivatives thereof, salts thereof, or mixtures thereof. While not limited to any particular mechanism, it is believed that these active agents may inactivate one or more of six Signal Transducers and Activators of Transcription (STAT) pathways. For example, STAT3 inhibitors may remedy psoriasis disease states with complete effectiveness. STAT5 or its pathway or any other of the STAT1 through STAT6 proteins and their pathways may also be blocked by the active agent to treat the skin. Further, interleukin 6 (IL-6) and interleukin 9 (IL-9) signaling may also be affected by the active agent during treatment.

The active agent, such as a caffeic acid compound or a mixture thereof, may further be combined with other mechanistic compounds which include cell differentiating agents, anti-proliferative agents, mitochondrial inhibitors, topical steroids, immunosuppressive compounds, JAK2 inhibitors, JAK3 inhibitors, parathyroid hormone-related protein (PTHrP) agonists, cell adhesion blockers, and combinations thereof. Examples of cell differentiating agents include a retinoid, such as retinoic acid, vitamin D, vitamin D analogs, or a phorbol ester. The term vitamin D collectively refers to a group of structurally similar chemicals and their metabolites which include alfacalcidol (1-hydroxycholecalciferol), calcitriol (1,25-dihydroxycholecalciferol), cholecalciferol (vitamin D3), dihydrotachysterol (DHT) and ergocalciferol (vitamin D2). The active metabolite of vitamin D, 1,25-$(OH)_2D_3$, has a wide range of nonclassical actions in the body, such as regulation of cell growth and differentiation modulation of the immune system. Vitamin D may be used in combination with caffeic acid compounds including STAT3 inhibitors such as caffeic acid ester compounds (e.g., CAPE or CABE) to be effective in the treatment of skin inflammatory and proliferation disorders such as psoriasis. The caffeic acid compounds may tend to stop an active lesion while the cell differentiating agent may lessen the likelihood of reactivation of the lesion to prevent recurrence.

In another embodiment, some exemplary topical agents that may be combined with the active agent, such as a caffeic acid compound or a mixture thereof, may include cell differentiating and anti-proliferative agents (e.g., retinoic acid, retinoids (tazarotene), vitamin D, or vitamin D analogs (calcipotriene)); mitochondrial inhibitors (e.g., anthraline (dithranol, chrysarobin, or coal tar)); topical steroids (e.g., clobetasol propionate, betamethasone, betamethasone dipropionate, halobetasol propionate, fluocinonide, diflorasone diacetate, mometasone furoate, halcinonide, desoximetasone, fluticasone propionate, flurandrenolide, triamcinolone acetonide, fluocinolone acetonide, hydrocortisone, hydrocortisone valerate, prednicarbate, desonide, or alclometasone dipropionate); immunosuppressive compounds (e.g., tacrolimus (FK-506)); JAK2 inhibitors (e.g., INCB18424); JAK3 inhibitors (e.g., CP-690,550); parathyroid hormone-related protein (PTHrP) agonists (e.g., PTH(1-34)); and cell adhesion blockers (e.g., pan-selectin antagonist bimosiamose).

The pharmaceutical composition containing the caffeic acid compound may be applied as topical dosages and have the form of ointments, pastes, creams, lotions, gels, powders, solutions, sprays, and transdermal patches. The active agents described herein may be mixed with a carrier, which may include excipients, preservatives, or buffers. Exemplary carriers include petroleum jelly and dimethyl sulfoxide (DMSO). These dosage forms can also include excipients such as animal and vegetable fats, oils, waxes, paraffins, starch, tragacanth, cellulose derivatives, polyethylene glycols, silicones, bentonites, silicic acid, talc, zinc oxide, water, or mixtures thereof. Other carriers known to those having skill in the art may also be used to advantage.

In some embodiments, a topical pharmaceutical composition contains the caffeic acid compound (e.g., caffeic acid ester compounds or caffeic acid amide compounds) at a concentration by weight within a range from about 0.01% to about 20%, preferably, from about 0.1% to about 15%, preferably, from about 1% to about 10%, more preferably, from about 3% to about 7%, and more preferably, from about 4% to about 6%. In one example, the topical pharmaceutical composition contains the caffeic acid compound at a concentration by weight of about 5%.

In other embodiments, the topical dosage forms may contain about 0.5% to about 20.0% by weight of the caffeic acid compounds described herein. The weight percent of the compounds described herein within the topical dosage forms may range from about 1.0% to about 15.0% or about 5.0% to about 11.0% by weight of the pharmaceutical composition. Treatment regimes with the topical dosage forms may occur daily, twice daily, three times daily, or four times daily for durations, for example, of three weeks or four weeks or until symptoms are no longer present. In some examples, the topical dosage contains the caffeic acid amide compound at a concentration of about 5% by weight of the pharmaceutical composition. In other examples, the topical dosage contains the caffeic acid ester compound at a concentration of about 5% by weight of the pharmaceutical composition.

Treatment regimes with the pharmaceutical composition or the topical dosage forms may occur daily, twice daily, three times daily or four times daily for durations, for example, of three weeks or four weeks or until symptoms or the lesion are no longer present.

In many embodiments, the pharmaceutical compositions containing the caffeic acid compounds (e.g., caffeic acid ester compounds or caffeic acid amide compounds) may be useful to treat various tumors which include solid tumors, such as breast cancer, head and neck cancer, melanoma, ovarian cancer, lung cancer, pancreatic cancer and prostate cancer, and blood tumors, such as multiple myeloma, leukemias (e.g., HTLV-1-dependent, acute myelogenous leukemia, or large granular lymphocyte leukemia), and lymphomas (e.g., EBV-related/Burkitt's, mycosis fungoides, cutaneous T-cell lymphoma, non-Hodgkin's lymphoma, and anaplastic large-cell lymphoma).

In alternative embodiments, the pharmaceutical compositions containing caffeic acid compounds (e.g., caffeic acid amide compounds and caffeic acid ester compounds), tyrphostin, tyrphostin analogues, and other active agent compounds useful for pharmaceutical compositions and methods for the topical treatment of proliferative and inflammatory skin disorders such as plaque psoriasis and atopic dermatitis and other disorders with a topical application of the pharmaceutical composition. Embodiments provide that the pharmaceutical composition may contain one or more active agent compounds having the generic chemical structure:

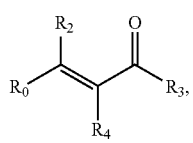

wherein $R_0$ may be selected from $R_1$ and $R_1—Z_1—$; and wherein $Z_1$ is alkyl; and
wherein $R_1$ may be selected from:

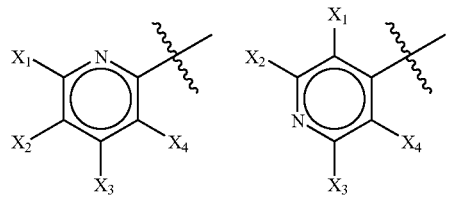

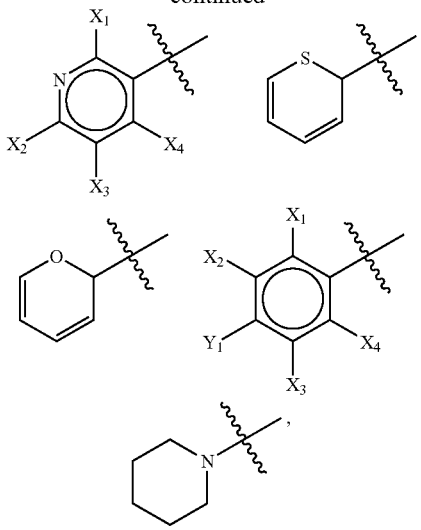

where $X_1$, $X_2$, $X_3$, and $X_4$, are each independently selected from hydrogen, halogen, alkyl, alkoxy, OH, trihalomethyl, or $NO_2$; where $Y_1$ may be selected from halogen or $NO_2$; and $R_2$ may be selected from alkyl, alkenyl, alkynyl, alkoxy, alkylaryl, halogen, hydrogen, OH, $NO_2$, thioether, amine, SH, or $NH_2$;

$R_3$ may be selected from:

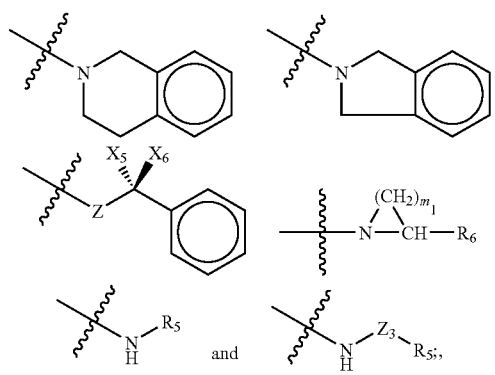

wherein $Z_3$ is alkyl; and wherein $m_1=1$, 2, 3, or 4; and where $R_4$ may be selected from: CN, substituted amine, $CH_2S$-alkyl, alkyl, and $CH_2N_3$; where $R_5$ and $R_6$ are each independently chosen from:

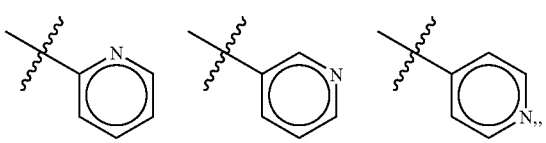

monosaccharide (e.g., glucose, fructose, galactose, etc.), polysaccharide, monosaccharide derivative (e.g., an acetylated monosaccharide such as acetylated galactose, 1,2,3,4-diisopropylideno-D-g-alactose) substituted and unsubstituted aryl, and substituted and unsubstituted alkylaryl; where Z may be selected from NH, S, and O, and where $X_5$ and $X_6$ are each independently chosen from hydrogen and lower alkyl.

In certain embodiments, $R_4$ is CN. In certain embodiments, $R_1$ may be chosen from:

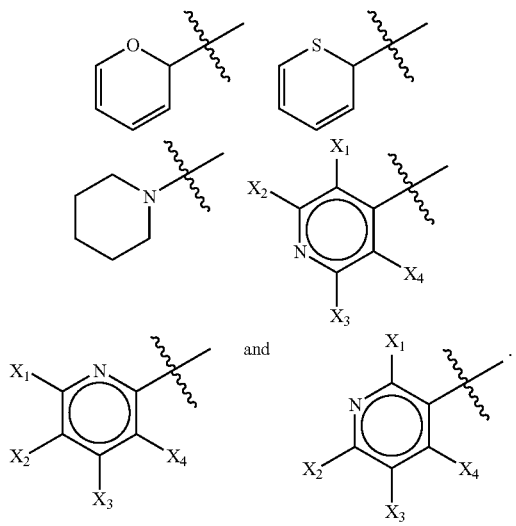

In more specific embodiments, $R_1$ may be:

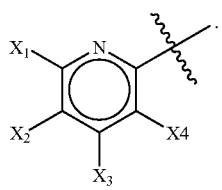

In certain embodiments, $X_1$ may be a halogen such as Br. $R_5$ may be chosen from an alkylaryl having the structure:

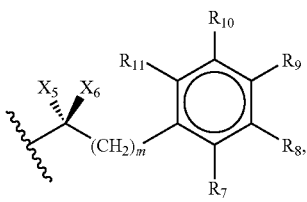

an aryl having the structure:

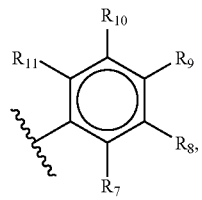

wherein m=0, 1, 2, 3, 4, 5, 6, or 7 and, where $X_5$ and $X_6$ are each independently chosen from hydrogen and alkyl, and where $R_7$, $R_8$, $R_9$, $R_{10}$, and $R_{11}$, are each independently selected from hydrogen, halogen, alkyl, alkoxy, OH, trihalomethyl, or $NO_2$.

In more specific embodiments $R_5$ is an alkylaryl. $X_1$, $X_2$, $X_3$, and $X_4$ may be hydrogen. $Z_1$ may be a lower alkyl, and the lower alkyl may be —$(CH_2)_{m3}$—, wherein m3=0, 1, 2, 3, or 4. $Z_3$ may be a lower alkyl, and the lower alkyl may be —$(CH_2)_{m4}$—, wherein m4=0, 1, 2, 3, or 4. $Y_1$ may be $NO_2$ or a halogen, such as Cl or Br.

In certain embodiments, $R_5$ may be selected from:

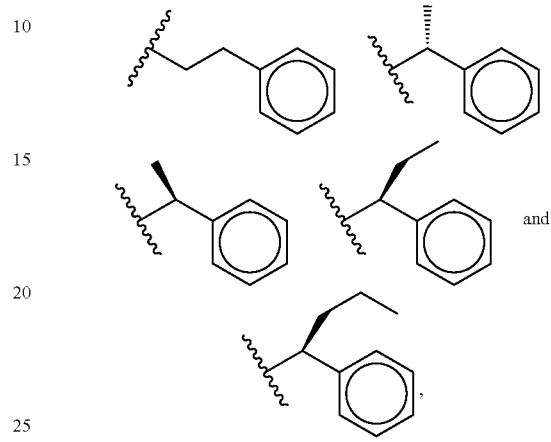

$R_2$ may be hydrogen. $Y_1$ may be selected from $NO_2$ and a halogen, such as Br or Cl.

In one example, the pharmaceutical compositions may contain an active agent or similar compound, such as the caffeic acid amide compound having the chemical structure of:

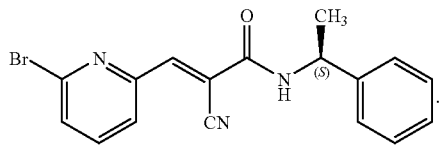

In another example, the pharmaceutical compositions may contain an active agent or similar compound, such as the caffeic acid amide compound having the chemical structure of:

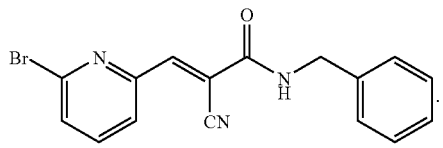 [SMILES: N#C/C(=C\c1cccc(Br)n1)C(=O)NCc1ccccc1]

In another example, the pharmaceutical compositions may contain an active agent or similar compound, such as the caffeic acid amide compound having the chemical structure of:

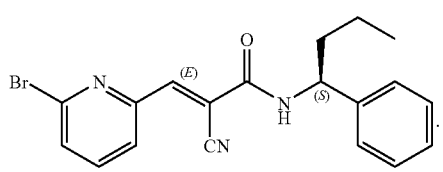

In another example, the pharmaceutical compositions may contain an active agent or similar compound, such as the caffeic acid amide compound having the chemical structure of:

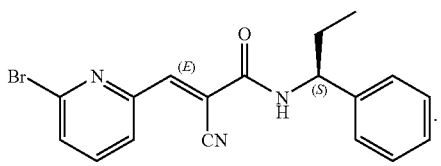

In another example, the pharmaceutical compositions may contain an active agent or similar compound, such as the caffeic acid amide compound having the chemical structure of:

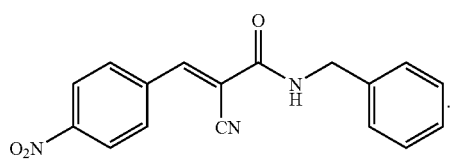 [SMILES: N#C/C(=C\c1ccc([N+](=O)[O-])cc1)C(=O)NCc1ccccc1]

In another example, the pharmaceutical compositions may contain an active agent or similar compound, such as the caffeic acid amide compound having the chemical structure of:

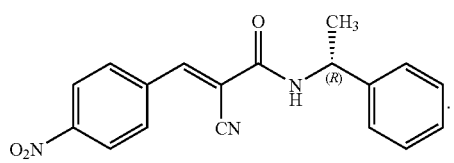

In another example, the pharmaceutical compositions may contain an active agent or similar compound, such as the caffeic acid amide compound having the chemical structure of:

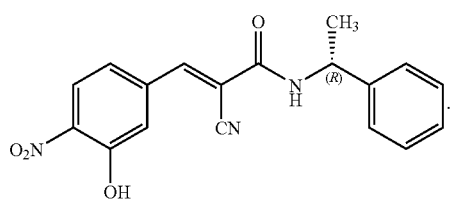

In another example, the pharmaceutical compositions may contain an active agent or similar compound, such as the caffeic acid amide compound having the chemical structure of:

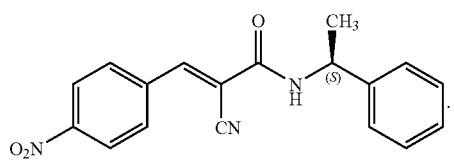

In another example, the pharmaceutical compositions may contain an active agent or similar compound, such as the caffeic acid amide compound having the chemical structure of:

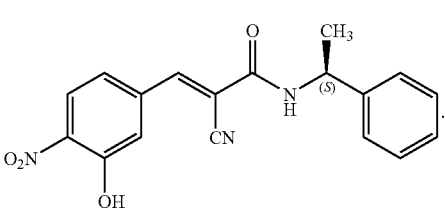

In another example, the pharmaceutical compositions may contain an active agent or similar compound, such as the caffeic acid amide compound having the chemical structure of:

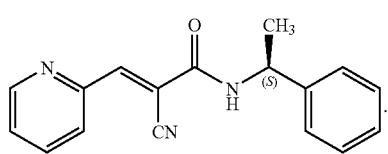

In another example, the pharmaceutical compositions may contain an active agent or similar compound, such as the caffeic acid amide compound having the chemical structure of:

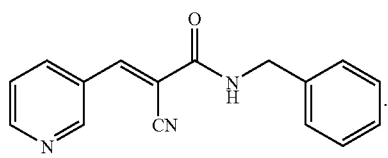 [SMILES: N#C/C(=C\c1cccnc1)C(=O)NCc1ccccc1]

In another example, the pharmaceutical compositions may contain an active agent or similar compound, such as the caffeic acid amide compound having the chemical structure of:

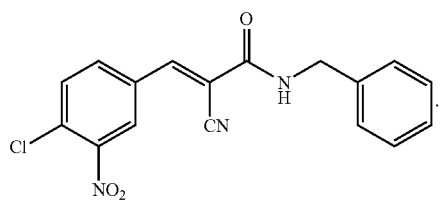 [SMILES: N#C/C(=C\c1ccc(Cl)c([N+](=O)[O-])c1)C(=O)NCc1ccccc1]

In other embodiments, the pharmaceutical compositions may contain active agents, such as the caffeic acid amide compounds having the following chemical structures:

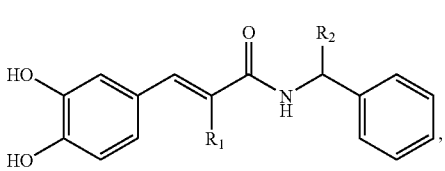

-continued

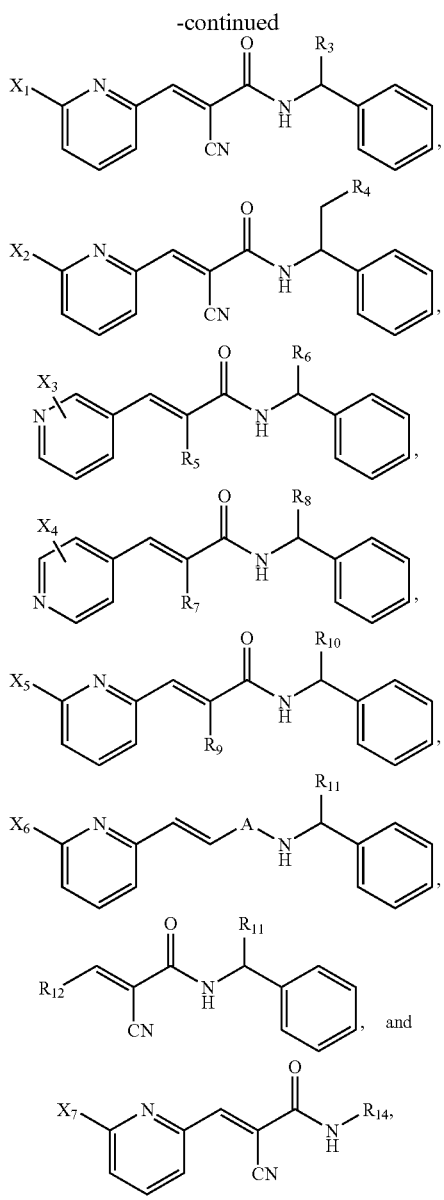

wherein $R_1$ may be —H or cyano and $R_2$ may be heteroatom-substituted or heteroatom-unsubstituted $C_3$-$C_7$-cycloalkyl;

$X_1$ may be halo and $R_3$ may be heteroatom-substituted or heteroatom-unsubstituted $C_1$-$C_7$-cycloalkyl, $C_6$-$C_{10}$-aryl, or $C_7$-$C_{10}$-aralkyl;

$X_2$ may be halo and $R_4$ may be hydroxy or heteroatom-substituted or heteroatom-unsubstituted $C_1$-$C_{10}$-acyloxy;

$X_3$ may be halo or heteroatom-substituted or heteroatom-unsubstituted $C_1$-$C_{10}$-alkyl or $C_1$-$C_{10}$-alkoxy; $R_5$ may be —H or cyano, and $R_6$ may be heteroatom-substituted or heteroatom-unsubstituted $C_1$-$C_{10}$-alkyl, $C_1$-$C_{10}$-acyloxy, $C_6$-$C_{10}$-aryl, or $C_7$-$C_{10}$-aralkyl;

$X_4$ may be halo or heteroatom-substituted or heteroatom-unsubstituted $C_1$-$C_{10}$-alkyl or $C_1$-$C_{10}$-alkoxy; $R_7$ may be H or cyano; $R_8$ may be heteroatom-substituted or heteroatom-unsubstituted $C_1$-$C_{10}$-alkyl, $C_1$-$C_{10}$-acyloxy, $C_6$-$C_{10}$-aryl, or $C_7$-$C_{10}$-aralkyl;

$X_5$ may be heteroatom-substituted or heteroatom-unsubstituted $C_1$-$C_{10}$-alkyl or $C_1$-$C_{10}$-alkoxy; $R_9$ may be —H or cyano; $R_{10}$ may be heteroatom-substituted or heteroatom-unsubstituted $C_1$-$C_{10}$-alkyl, $C_1$-$C_{10}$-acyloxy, aryl, or $C_7$-$C_{10}$-aralkyl; A may be —C(O)— or —S(O$_2$)—;

$X_6$ may be halo or heteroatom-substituted or heteroatom-unsubstituted $C_1$-$C_{10}$-alkyl or $C_1$-$C_{10}$-alkoxy; $R_{11}$ may be heteroatom-substituted or heteroatom-unsubstituted $C_1$-$C_{10}$-alkyl, $C_1$-$C_7$-cycloalkyl, $C_1$-$C_{10}$-acyloxy, $C_6$-$C_{10}$-aryl, or $C_7$-$C_{10}$-aralkyl; $R_{12}$ may be cyclododecyl, imidazoyl, or cyclohexenyl; $R_{13}$ may be —H or heteroatom-substituted or heteroatom-unsubstituted $C_1$-$C_{10}$-alkyl, $C_1$-$C_7$-cycloalkyl, $C_1$-$C_{10}$-acyloxy, $C_6$-$C_{10}$-aryl, or $C_7$-$C_{10}$-aralkyl;

$X_7$ may be halo or heteroatom-substituted or heteroatom-unsubstituted $C_1$-$C_{10}$-alkyl or $C_1$-$C_{10}$-alkoxy; $R_{14}$ may be:

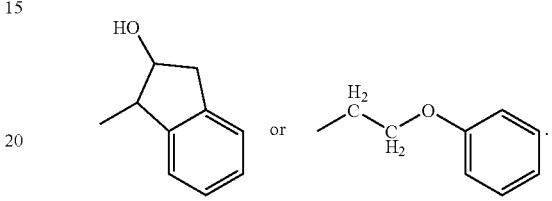

Other aspects of the invention include pharmaceutically acceptable salts, hydrates, amine-N-oxides, imine-N-oxides, tautomers, and optical isomers of the compounds described above and throughout this application.

In certain embodiments $R_2$ may cyclopropyl, cyclobutyl, cyclopentyl or cyclohexyl. In further embodiments $R_3$ may be phenyl, benzyl, cyclopropyl, cyclobutyl, cyclopentyl or cyclohexyl. In yet further embodiments, $X_1$ or $X_2$ may be —F, —Cl, —Br or —I. In still further embodiments, $R_4$ may be hydroxy, acetoxy or 2,2-dimethylpropionyloxy. In still yet further embodiments, $X_3$ or $X_4$ may be methoxy, —F, —Cl, —Br or —I. In some embodiments, $R_6$ or $R_8$ may be methyl or cyclopropyl. In certain aspects, $X_5$ may be methyl or acetoxymethyl.

In other embodiments, the pharmaceutical compositions may contain active agents, such as the caffeic acid compounds having the following chemical structures:

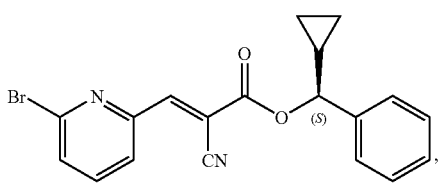
(WP1332)

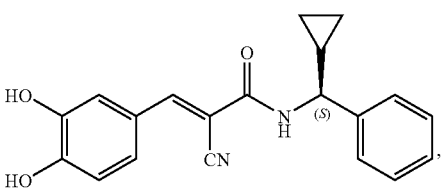
(WP1331)

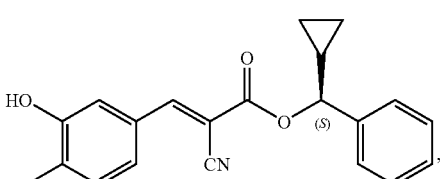
(WP1330)

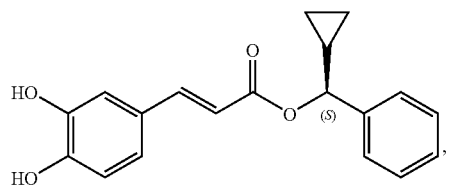
(WP1329)
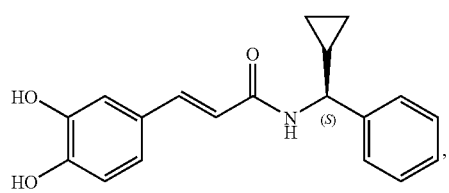
(WP1328)
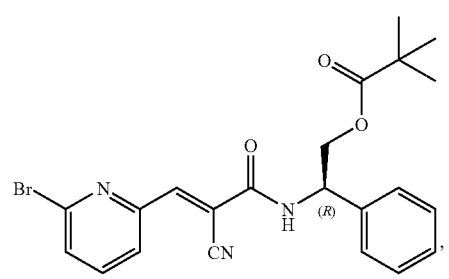
(WP1302)
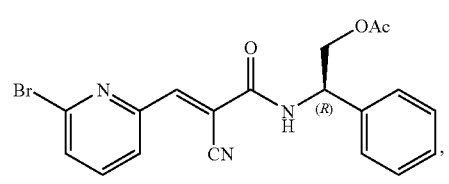
(WP1293)
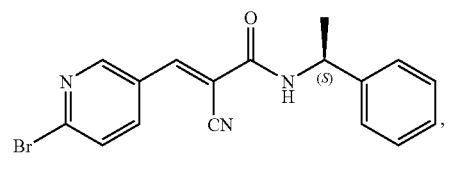
(WP1286)
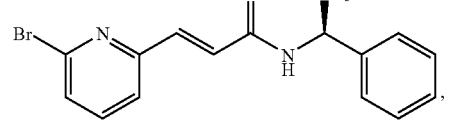
(WP1285)
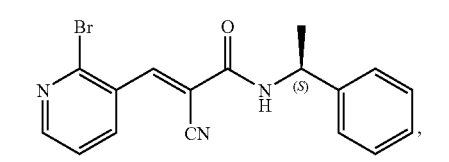
(WP1284)
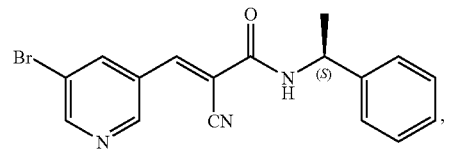
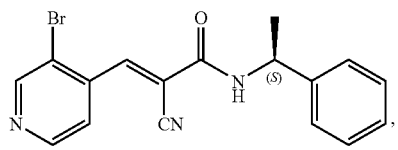
(WP1283)
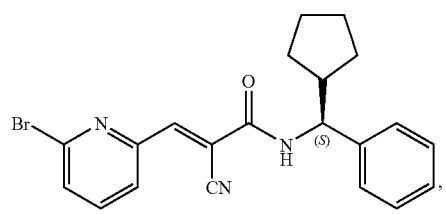
(WP1282)
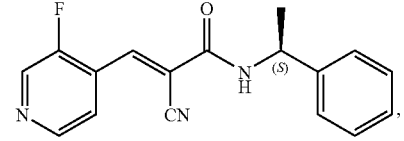
WP1280
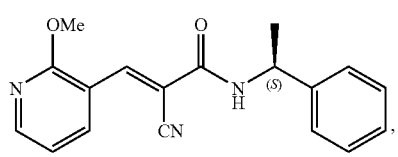
(WP1273)
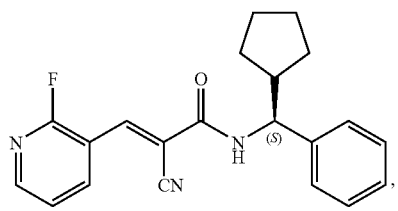
(WP1272)
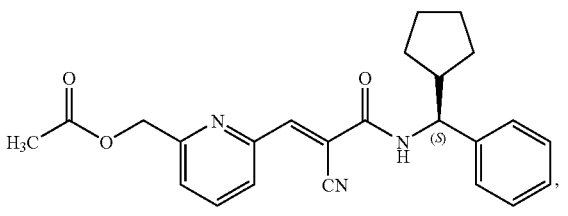
(WP1246)
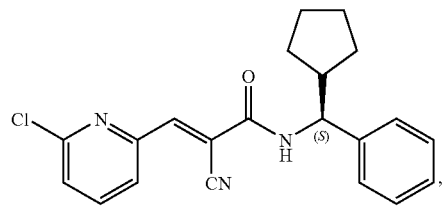
(WP1229)
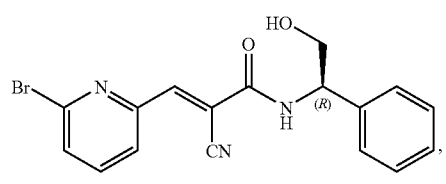
(WP1269)

-continued (WP1271)

(WP1268)

(WP1267)

(WP1203)

(WP1201)

(WP1196)

(WP1180)

(WP1179)

-continued (WP1169)

(WP1168)

(WP1167)

(WP1166)

(WP1164)

(WP1163)

(WP1159).

Some of the aforementioned caffeic acid compounds are shown as single enantiomers or diastereomers. Embodiments provide for all possible stereoisomers of any of the caffeic acid compounds above, as well as those described throughout the application. In some embodiments, the caffeic acid compound may be a single enantiomer substantially free from other stereoisomers. In other embodiments, the caffeic acid compound may be a mixture of different stereo isomers, wherein each stereo isomer has the same molecular formula. Embodiments provide for a racemic mixture of a given molecular formula.

In other embodiments of the invention, the pharmaceutical compositions may contain active agents or similar compounds having the chemical formula:

wherein A is —C(O)— or —SO$_2$—. In certain embodiments R$_1$ is cyclododecyl,

In some of these embodiments, X$_1$, X$_2$, X$_3$, and X$_4$, are each independently hydrogen, halo, alkyl, alkoxyl, acetoxyl, alkylacetoxyl, —OH, trihalomethyl, or —NO$_2$; Y$_1$ is halo, —OH or —NO$_2$; and R$_2$ may be selected from alkyl, alkenyl, alkynyl, alkoxy, alkylaryl, halo, hydrogen, —OH, —NO$_2$, thioether, amino, —SH, or —NH$_2$; R$_3$ is:

wherein Z$_3$ may be a divalent alkyl; and wherein m$_1$=1, 2, 3, or 4; and R$_4$ may be hydrogen, —CN, substituted amine, —CH$_2$S-alkyl, alkyl, or —CH$_2$N$_3$. In some of these embodiments, R$_5$ and R$_6$ are each independently:

monosaccharide, monosaccharide derivative, polysaccharide, polysaccharide derivative, aryl or aralkyl; Z may be selected from —NH, —S—, or —O—, and $X_5$ and $X_6$ may independently be selected from hydrogen, upper alkyl, lower alkyl, cycloalkyl, cycloarylalkyl, aralkyl, aryl, alkoxyl, hydroxyl, hydroxylalkyl, alkylester, alkylesteralkyl, alkylacetoxyl, or aryloxyl; with the proviso that if $R_4$.dbd.-CN, substituted amine, —$CH_2$S-alkyl, alkyl, or —$CH_2N_3$, then $R_1$ may be selected from cyclododecyl,

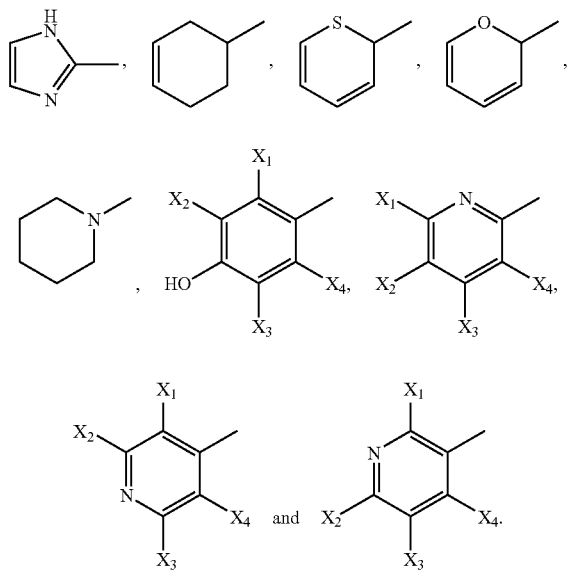

In other embodiments, $R_3$ may be:

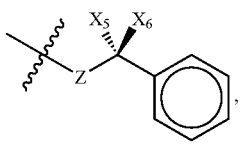

where $X_5$ or $X_6$ is upper alkyl, hydroxyl, aryl, alkoxyl, aryloxyl; cycloalkyl, cycloarylalkyl, aralkyl, alkylester, alkylesteralkyl, alkylacetoxy, or aryloxyl.

In specific embodiments, $Z_3$ may be —$C_2H_4$—. In some examples, $X_1$, $X_2$, $X_3$, and $X_4$, are each independently —F, —Cl—, —Br, —$CH_3$, methoxy or alkylacetoxyl. In further embodiments, $X_5$ or $X_6$ is independently hydrogen, cyclopropyl, cyclobutyl, —$CH_3$, —$CH_2OH$, cyclopentyl, —$CH_2OAc$, —$CH_2OC(O)C(CH_3)_3$, —$CH_2C_6H_5$, cyclohexyl or aryl.

In other embodiments, $R_5$ is an aralkyl having the structure:

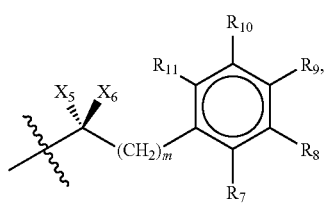

and an aryl having the structure:

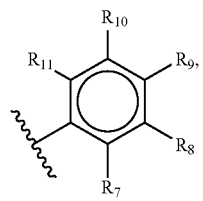

wherein m=0, 1, 2, 3, 4, 5, 6, or 7 and where $X_5$ and $X_6$ may each independently be selected from hydrogen or alkyl, and where $R_7$, $R_8$, $R_9$, $R_{10}$, and $R_{11}$ may each independently be selected from hydrogen, halo, alkyl, alkoxy, —OH, trihalomethyl, or —$NO_2$.

Embodiments heretofore relate to pharmaceutical compositions and methods for treating psoriasis and similar skin disorders. However, embodiments of the invention may be utilized for other skin disorders and may benefit from the caffeic acid compounds described herein that inhibit cell proliferation. While the foregoing is directed to embodiments of the invention, other and further embodiments of the invention may be devised without departing from the basic scope thereof, and the scope thereof is determined by the claims that follow.

What we claim is:

1. A pharmaceutical composition for topical application to psoriatic lesions, comprising:
   a carrier suitable for topical administration; and
   a caffeic acid amide compound having the chemical structure:

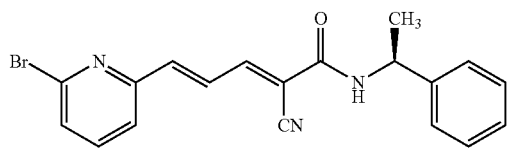 [SMILES: C[C@H](NC(=O)/C(C#N)=C/C=C/c1cccc(Br)n1)c1ccccc1]

wherein the caffeic acid amide compound is present at a concentration by weight within a range from about 0.01% to about 20% of the pharmaceutical composition.

2. The pharmaceutical composition of claim 1, wherein the topical pharmaceutical composition comprises the caffeic acid amide compound at a concentration by weight within a range from about 1% to about 10%.

3. The pharmaceutical composition of claim 2, wherein the topical pharmaceutical composition comprises the caffeic acid amide compound at a concentration by weight within a range from about 3% to about 7%.

4. The pharmaceutical composition of claim 1, further comprising petroleum jelly or dimethyl sulfoxide.

5. The pharmaceutical composition of claim 1, further comprising at least one compound selected from the group consisting of cell differentiating agents, anti-proliferative agents, mitochondrial inhibitors, topical steroids, immunosuppressive compounds, JAK2 inhibitors, JAK3 inhibitors, parathyroid hormone-related protein (PTHrP) agonists, cell adhesion blockers, and combinations thereof.

6. The pharmaceutical composition of claim 1, further comprising a cell differentiating agent selected from at least one of retinoic acid, retinoic acid derivative, vitamin D, or vitamin D analog.

* * * * *